US 6,717,025 B1

(12) United States Patent
Risch et al.

(10) Patent No.: US 6,717,025 B1
(45) Date of Patent: Apr. 6, 2004

(54) PROCESS FOR REMOVING OXYGENATES FROM AN OLEFINIC STREAM

(75) Inventors: Michael A. Risch, Seabrook, TX (US); Teng Xu, Houston, TX (US); John Di-Yi Ou, Houston, TX (US); Keith Holroyd Kuechler, Friendswood, TX (US); James H. Beech, Kingwood, TX (US); James Richardson Lattner, Seabrook, TX (US); Cor F. Van Egmond, Pasadena, TX (US)

(73) Assignee: ExxonMobil Chemical Patents Inc, Houston, TX (US)

( * ) Notice: Subject to any disclaimer, the term of this patent is extended or adjusted under 35 U.S.C. 154(b) by 0 days.

(21) Appl. No.: 10/295,066

(22) Filed: Nov. 15, 2002

(51) Int. Cl.⁷ .............................................. C07C 7/148
(52) U.S. Cl. ...................... 585/804; 585/638
(58) Field of Search .................. 585/804, 638

(56) References Cited

U.S. PATENT DOCUMENTS

| 4,367,653 A | 1/1983 | Richter et al. ............ 73/831.21 |
| 4,587,373 A | 5/1986 | Hsia ........................... 585/639 |
| 4,625,050 A | 11/1986 | Current ....................... 560/232 |
| 4,912,281 A | 3/1990 | Wu .............................. 585/640 |
| 5,491,273 A | 2/1996 | Santiesteban et al. ....... 585/639 |
| 5,837,217 A | 11/1998 | Nielsen et al. ........... 423/648.1 |
| 6,084,140 A | 7/2000 | Kitamura et al. ........... 585/260 |

FOREIGN PATENT DOCUMENTS

| DE | 27 20 749 | 9/1977 | ............. C07C/1/24 |
| DE | 32 10 756 | 3/1982 | ............. C07C/1/24 |
| EP | 0 229 994 | 3/1989 | ............. C07C/7/13 |

OTHER PUBLICATIONS

Engelen et al., "The Conversion of Dimethylether Over Pt/H–ZSm5. A Bifunctional Catalzyed Reaction." *Catalysts by Acids and Bases*, Elsevier Science Publishers, Amsterdam, pp. 391–398 (1985).

Chen et al., "The Role of Sillover in Hydrogenation of Oxygenates Absorbed on Ni/Al203", New Aspects of Spillover Effect in Catalysis, Elsevier Science Publishers, pp. 171–175 (1993).

*Primary Examiner*—Thuan D. Dang

(57) ABSTRACT

The present invention provides a process for removing oxygenate impurities, e.g., dimethyl ether, from an olefinic product stream by converting the oxygenate impurity to a compound whose boiling point differs by at least about 5° C. from the oxygenate impurity. Typically, the compound is more readily removable from the product stream than the oxygenate impurity.

71 Claims, 3 Drawing Sheets

PROCESS FOR REMOVING OXYGENATES FROM AN OLEFINIC STREAM

FIELD OF THE INVENTION

The present invention relates to a method for removing oxygenates from an olefinic stream by converting the oxygenates in the presence of a catalyst to higher or lower boiling compounds which are more readily separable from the stream, and then removing the higher or lower boiling compounds from the stream.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

The conversion of oxygenates to olefins generates by-products whose presence is undesirable for subsequent applications of the collected olefins. Although the separation of many oxygenates, e.g., ketones and aldehydes, from hydrocarbons such as olefins can be capably handled by existing commercial processes, the separation of other oxygenates, e.g., dimethyl ether (DME) can be problematic. DME is an oxygenate impurity formed during the conversion of methanol into light olefins which can act as a poison to downstream olefin polymerization catalysts, especially metallocene catalysts. Removal of DME from oxygenates to olefins product streams is thus highly desirable. Unfortunately, such removal can be difficult given, inter alia, DME's physical characteristics similar to certain lower olefins, e.g., its similar volatility to propylene. Separation of DME from propylene by distillation, e.g., using a $C_3$ splitter, requires a super fractionation column requiring significant capital investment. Alternatively, DME's difference in solubility from lower olefins can be exploited by using a water wash to remove DME from an olefinic product stream. Unfortunately, given DME's non-polar characteristics, an extensive volume of water would be required in a water wash tower so employed. Given these difficulties it would be desirable to provide a process for removing DME from olefin-containing streams such as those obtained by conversion of oxygenates to olefins, which does not require superfractionation or water washing.

Methods for recovering and recycling dimethyl ether (DME) from a methanol-to-chemical conversion reaction using a DME absorber tower is disclosed in U.S. Pat. No. 4,587,373 to Hsia.

Stud. Surf. Sci. Catal. (1985), 20 (Catl. Acids Bases), 391–8, discusses low temperature conversion of dimethyl ether over Pt/H-ZSM-5 in the presence of hydrogen by a bifunctional catalyzed reaction.

Stud. Surf. Sci. Catal. (1993), 77 discusses hydrogenation of oxygenates such as dimethyl ether over a $Ni/Al_2O_3$ catalyst to form methane.

U.S. Pat. No. 5,491,273 to Chang et al. discloses conversion of lower aliphatic alcohols and corresponding ethers to linear olefins over large crystal zeolites, e.g., ZSM-35 containing a hydrogenation component of Group VIA and Group VIIIA metals.

DE3210756 discloses a process for converting methanol and/or dimethyl ether feed to olefins by reacting the feed over a pentasil-type zeolite catalyst, separating $C_2$–$C_4$ olefins, methane and water from the reaction product and catalytically hydrogenating the remaining components over Co—Mo supported on alumina, optionally preceded by hydrogenation over a Gp. 8 noble metal for polyunsaturated, non-aromatic compounds.

U.S. Pat. No. 4,912,281 to Wu discloses converting methanol or methyl ether to light olefins in the presence of hydrogen and ZSM45 which is highly selective to $C_2$–$C_4$ olefins, especially ethylene.

DE2720749 discloses converting lower aliphatic ethers to hydrocarbons in the presence of amorphous, non-acid-activated Al silicate.

U.S. Pat. No. 4,625,050 to Current discloses the use of carbonylation to convert dimethyl ether to methyl acetate and ethanol (as well as minor amounts of methyl formate and propanol) over hydrogen and CO in the presence of heterogeneous NiMo catalyst on an alumina support.

EP-229994 discloses the removal of DME as an impurity (1–500 wppm) of olefinic hydrocarbon feedstock by passing the feedstock through an adsorbent mass of crystalline zeolite molecular sieve having the crystal structure of faujasite at 0–60° C. and 0.15–500 psia to selectively absorb DME.

In addition to DME, light olefin products, especially those generated by steam cracking or derived from oxygenated feedstocks, can contain unsaturated by-products such as acetylene, methylacetylene (MA) and propadiene. Making olefins from oxygenated feedstocks produces a unique effluent stream that must ultimately be separated and purified to produce the high purity olefin products currently desired. These unsaturated by-products poison polyolefin catalysts, and therefore must be almost completely removed from olefin product streams. For ethylene, current manufacturing specifications can require acetylene levels to be under 0.5 mole ppm. For propylene, current manufacturing specifications can require methyl acetylene and propadiene levels to be under 2.9 mole ppm.

Catalysts for selectively hydrogenating highly unsaturated compounds are known in the art. For example, U.S. Pat. No. 6,084,140 to Kitamura et al. discloses a palladium and alumna catalyst for hydrogenating highly unsaturated hydrocarbons in olefin streams from steam cracking processes. The catalyst can hydrogenate acetylene, methyl acetylene, and propadiene, with only limited hydrogenation of the olefin products. U.S. Pat. No. 4,367,353 to Inglis discusses a hydrogenation process using a supported palladium catalyst. The process involves first fractionating the hydrocarbon streams before hydrogenating, whereby hydrogen is removed. Hydrogen is added during a subsequent hydrogenation step, allowing for greater control of the extent of hydrogenation. Because the concentration of unsaturated by-products acetylene, methyl acetylene, and propadiene can increase to three times their initial amounts during the purification of the hydrocarbons by fractionation, the concentration of acetylene, methyl acetylene and propadiene must be three times lower following front-end hydrogenation than in tail end hydrogenation. Achieving this greater purity results in greater loss of olefin products during the hydrogenation process.

U.S. Pat. No. 5,837,217 to Nielsen et al. discloses preparation of hydrogen rich gas from a feed stock of dimethyl ether and steam, wherein the dimethyl ether is reacted with steam in the presence of i) an ether hydration catalyst such as acidic zeolites, e.g. HZSM-5, and ii) a methanol decomposition catalyst, e.g., Cu—Zn-alumina.

Given the difficulties presented in separately removing by-products DME and the unsaturated compounds methyl acetylene, propadiene and acetylene from olefinic product streams, particularly those product streams from steam cracking and oxygenate to olefins processes, it would be advantageous to remove at least one or more of these by-products with techniques that do not require dedicated equipment for superfractionation, water washing, etc. Moreover, it would be advantageous to at least partially remove these by-products using equipment commonly found in existing olefin plant recovery trains, e.g., hydrogenation reactors. Accordingly, it would be particularly advantageous to remove DME along with the hydrocarbon impurities acetylene, methyl acetylene, and propadiene from product streams using the same equipment.

SUMMARY OF THE INVENTION

In one aspect, the present invention relates to a process for at least partially removing from a product stream comprising $C_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethyl isopropyl ether, n-propylisopropyl ether, or mixtures thereof which comprises: converting said oxygenate impurity to a compound whose boiling point differs by at least about 5° C. from said oxygenate impurity; and separating at least some of said compound from said $C_x$ olefin.

In one embodiment of this aspect of the invention, the oxygenate impurity comprises dimethyl ether.

In another embodiment of this aspect of the invention, the product stream comprises at least about 1 mppm dimethyl ether, e.g., at least about 2.5 wt % dimethyl ether. As used herein and in the claims, the term "mppm" represents parts per million of a given component in a given stream on a molar basis.

In another embodiment of this aspect, the separating provides an oxygenate impurity-depleted stream which comprises no greater than about 100 mppm dimethyl ether, preferably no greater than about 50 mppm dimethyl ether, more preferably no greater than about 10 mppm dimethyl ether, say, no greater than about 1 mppm dimethyl ether.

In another embodiment of this aspect of the invention, the product stream comprises propylene.

In still another embodiment of this aspect of the invention, the separating is carried out by fractionating in a distillation column.

In yet another embodiment of this aspect of the invention, the converting is carried out without substantially converting said $C_x$ olefin, i.e., no greater than about 5%, preferably no greater than about 2%, even more preferably no greater than about 0.1% of said $C_x$ olefin is converted to non-$C_x$ olefin compounds.

In still yet another embodiment of this aspect of the invention, the converting is carried out in the absence of added hydrogen.

In another embodiment of this aspect of the invention, the converting is carried out in the presence of added hydrogen.

In yet another embodiment of this aspect of the invention, the product stream comprises at least one member selected from the group consisting of methanol, water, CO and $CO_2$, wherein said product stream is treated to remove at least some of said member, prior to said converting.

In still another embodiment of this aspect of the invention, the product stream containing said oxygenate impurity is derived from a process which converts oxygenates to olefins.

In yet another embodiment of this aspect of the invention, the boiling point differs by at least about 10° C., preferably by at least about 25° C., more preferably by at least about 50° C.

In another aspect of this invention, the present invention relates to a process for at least partially removing from a product stream comprising $C_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethylisopropyl ether, n-propylisopropyl ether, or mixtures thereof which comprises: converting said oxygenate impurity to a compound whose boiling point is at least about 5° C. lower than said oxygenate impurity; and separating at least some of said compound from said $C_x$ olefin.

In one embodiment of this aspect of the invention, the boiling point of said compound is at least about 5° C., typically at least about 10° C., say, at least about 25° C., e.g., at least about 50° C., lower than said oxygenate impurity and the converting step comprises contacting at least a portion of said product stream with a catalyst comprising a member selected from the group consisting of metal and metal compound. Typically, the catalyst comprises at least one member selected from the group consisting of group 3 (IIIA) metal, group 3 (IIIA) metal compound, group 4 (IVA) metal, group 4 (IVA) metal compound, group 5 (VA) metal, group 5 (VA) metal compound, group 6 (VIA) metal, group 6 (VIA) metal compound, group 7 (VIIA) metal, group 7 (VIIA) metal compound, group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, group 11 (IB) metal compound, group 12 (IIB) metal, and group 12 (IIB) metal compound.

In an embodiment of this aspect of the invention, the oxygenate impurity comprises dimethyl ether and said converting is carried out under conditions sufficient to convert said dimethyl ether to a mixture containing a member selected from the group consisting of methane, CO and $CO_2$.

In another aspect of this invention, the catalyst comprises a member selected from the group consisting of group 11 (IB) metal and group 11 (IB) metal compound, e.g., Ag or a compound thereof, or copper or a compound thereof.

In yet another embodiment of this aspect of the invention, the catalyst comprises a group 11 (IB) metal or metal compound and an inorganic oxide, e.g., silver supported on alumina. Typically, the inorganic oxide support comprises at least one oxide selected from the group consisting of oxides of elements of groups 2–5, inclusive, Zn, groups 13, 14 (excluding carbon), and 15 (excluding nitrogen).

In still another embodiment of this aspect of the invention, the catalyst is a methanol synthesis catalyst, typically one which comprises copper, zinc oxide and alumina.

In still yet another embodiment of this aspect of the invention, no greater than about 1 wt %, say, no greater than about 0.1 wt % of said $C_x$ olefin is converted by said converting step.

In another embodiment of this aspect of the invention, the conditions sufficient to convert said dimethyl ether comprise temperatures ranging from about 300° to about 550° C., and pressures ranging from about 60 to about 3500 kPaa.

In another aspect of this invention, the present invention relates to a process for at least partially removing from a product stream comprising $C_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethylisopropyl ether, n-propylisopropyl ether, or mixtures thereof which comprises: converting said oxygenate impurity to a compound whose boiling point is at least about 5° C., typically at least about 10°C., say, at least about 25° C., e.g., at least about 50° C., higher than said oxygenate impurity; and separating at least some of said compound from said $C_x$ olefin. Typically, the converting comprises contacting at least a portion of said product stream with a supported metal catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) a member selected from the group consisting of a porous inorganic oxide and microporous crystalline molecular sieve, said converting taking place at conditions sufficient to convert said oxygenate impurity to at least one higher boiling compound.

In one embodiment of this aspect of the invention, the converting is carried out in the absence of added hydrogen.

In an alternative embodiment of this aspect of the invention, the converting is carried out in the presence of added hydrogen.

In another embodiment of this aspect of the invention, the contacting is carried out in the presence of hydrogen and said supported metal catalyst is a hydrogenation catalyst.

In still another embodiment of this aspect of the invention, the contacting is carried out in the absence of hydrogen.

In another aspect, the present invention relates to a process for at least partially removing from a product stream comprising $C_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethylisopropyl ether, n-propylisopropyl ether, or mixtures thereof which comprises: converting said oxygenate impurity to a compound whose boiling point is at least about 5° C., typically at least about 10° C., say, at least about 25° C., e.g., at least about 50° C., higher than said oxygenate impurity; and separating at least some of said compound from said $C_x$ olefin. Typically, the converting comprises contacting at least a portion of said product stream with a supported metal catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) a member selected from the group consisting of a porous inorganic oxide and microporous crystalline molecular sieve, said converting taking place at conditions sufficient to convert said oxygenate impurity to at least one higher boiling compound. The product stream comprises highly unsaturated $C_2$ to $C_4$ by-products comprising a member selected from the group consisting of an alkyne and an alkadiene. Optionally, additional amounts of a member selected from the group consisting of alkyne and alkadiene can be added as necessary, to react during said converting with unreacted oxygenate.

In one embodiment of this aspect of the invention, the alkyne comprises a member selected from the group consisting of acetylene, methyl acetylene, ethyl acetylene and dimethyl acetylene, and the alkadiene comprises a member selected from the group consisting of propadiene, 1,2-butadiene and 1,3-butadiene.

In another embodiment of this aspect of the invention, the $C_2$ olefin fraction of the product stream or stream derived therefrom comprises at least 1 mppm of acetylene.

In still another embodiment of this aspect of the invention, the $C_3$ olefins fraction of said product stream or stream derived therefrom comprises at least 1 mppm of methyl acetylene and/or at least 1 mppm of propadiene.

In yet another embodiment of this aspect of the invention, the $C_4$ olefins fraction of the product stream or stream derived therefrom comprises at least 1 mppm of a member selected from the group consisting of ethyl acetylene, dimethyl acetylene, 1,2-butadiene and 1,3-butadiene.

In still yet another embodiment of this aspect of the invention, the converting provides at least partial hydrogenation of the member selected from the group consisting of alkyne and alkadiene by at least about 20%. The at least partial hydrogenation typically provides a member selected from the group consisting of ethylene, propylene and butene.

In yet another embodiment of this aspect of the invention, the oxygenate impurity comprises dimethyl ether. Typically, the $C_3$ to $C_4$ olefin fraction of said product stream or stream derived therefrom contains at least about 1 mppm oxygenates comprising dimethyl ether. The catalyst typically comprises at least one member selected from the group consisting of group 10 (VIII) and group 11 (1B) metals.

In another embodiment of this aspect of the invention, the catalyst comprises palladium.

In another embodiment of this aspect of the invention, the catalyst comprises silver.

In yet another embodiment of this aspect of the invention, the catalyst comprises palladium and silver.

In still another embodiment of this aspect of the invention, the catalyst comprises at least one of i) at least one porous inorganic oxide selected from the group consisting of silica, alumina, silica-alumina, zirconia, titania, aluminophosphate and clay, and ii) at least one microporous crystalline molecular sieve selected from the group consisting of silicates, aluminosilicates, substituted aluminosilicates, aluminophosphates, and substituted aluminophosphates. The catalyst optionally comprises iii) a member selected from the group consisting of a sulfur-containing moiety and oxygen-containing moiety.

In yet another embodiment of this aspect of the invention, the converting step is carried out in the liquid phase and comprises a temperature ranging from about 20° C. to about 100° C., total pressures ranging from about 1140 kPaa to about 4240 kPaa (from about 150 psig to about 600 psig), LHSV ranging from about 0.1 to about 100, and a hydrogen/(alkyne+alkadiene) ratio ranging from about 0.1 to about 100 on a molar basis.

In still another embodiment of this aspect of the invention, the converting conditions are carried out in the vapor phase and comprise a temperature ranging from about 20° C. to about 600° C., total pressures ranging from about 102 kPaa to about 4240 kPaa (from about 0.1 psig to about 600 psig), GHSV ranging from about 100 to about 20,000, and hydrogen partial pressure ranging from about 0.001 psig to about 200 psig.

In yet another embodiment of this aspect of the invention, the higher boiling compound is selected from at least one of acetone and methyl isopropyl ether.

In yet another embodiment of this aspect of the invention, at least 20%, typically at least about 50%, say, at least about 80%, of said dimethyl ether in the product stream is converted during the converting step.

Another aspect of the present invention relates to a process for at least partially removing dimethyl ether from a propylene-containing olefins stream which comprises converting at least a portion of said stream over a catalyst comprising metal and/or metal oxide, under conditions sufficient to selectively decompose said dimethyl ether to a mixture of methane, CO and $CO_2$, in the presence of said olefins without substantially converting said olefins.

In one embodiment of this aspect of the invention, the catalyst comprises silver supported on alumina.

In another embodiment of this aspect of the invention, the catalyst comprises copper, zinc oxide and alumina.

In yet another embodiment of this aspect of the invention, the converting step is carried out in the absence of added hydrogen.

Another aspect of this invention relates to a process for at least partially removing oxygenate impurities from an olefin-containing stream produced by an oxygenate to olefin process which comprises: contacting an oxygenate feedstream with an olefin generation catalyst under conditions sufficient to provide a first product stream which contains $C_2$ to $C_4$ olefins, $C_2$ to $C_4$ paraffins, hydrogen, methane, oxygenates comprising dimethyl ether, and highly unsaturated $C_2$ to $C_4$ by-products comprising a member selected from the group consisting of an alkyne and an alkadiene; exposing at least a portion of the product stream or stream derived therefrom to a supported metal catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of a porous inorganic oxide and microporous crystalline molecular sieve, said exposing taking place at conditions sufficient to convert said dimethyl ether to at least one higher boiling product; and removing at least some of said higher boiling product.

In an embodiment of this aspect of the invention, the exposing is carried out in the presence of hydrogen and said supported metal catalyst is a hydrogenation catalyst.

In another embodiment of this aspect of the invention, the exposing is carried out in the absence of hydrogen.

In still another embodiment of this aspect of the invention, the $C_3$ to $C_4$ olefin fraction of said product stream or stream derived therefrom contains at least 1 mppm oxygenates comprising dimethyl ether.

In yet another embodiment of this aspect of the invention, the alkyne comprises a member selected from the group consisting of acetylene, methyl acetylene, ethyl acetylene and dimethyl acetylene, and said alkadiene comprises a member selected from the group consisting of propadiene, 1,2-butadiene and 1,3-butadiene. The $C_2$ olefin fraction of the product stream or stream derived therefrom typically comprises at least 1 mppm of acetylene, the $C_3$ olefins fraction of the product stream or stream derived therefrom typically comprises at least 1 mppm of methyl acetylene and/or at least 1 mppm of propadiene, and the $C_4$ olefins fraction of the product stream or stream derived therefrom comprises at least 1 mppm of a member selected from the group consisting of ethyl acetylene, dimethyl acetylene, 1,2-butadiene and 1,3-butadiene.

In still yet another embodiment of this aspect of the invention, the catalyst comprises a member selected from the group consisting of group 10 (VIII) and group 11 (IB) metals, e.g., palladium, or silver, or palladium and silver.

In another embodiment of this aspect of the invention, the catalyst comprises at least one of i) at least one porous inorganic oxide selected from the group consisting of silica, alumina, silica-alumina, zirconia, titania, aluminophosphate and clay, and ii) at least one microporous crystalline molecular sieve selected from the group consisting of silicates, aluminosilicates, substituted aluminosilicates, aluminophosphates, and substituted aluminophosphates. The catalyst can further comprise iii) a member selected from the group consisting of a sulfur-containing moiety and oxygen-containing moiety.

In still another embodiment of this aspect of the invention, the exposing conditions are carried out in the liquid phase and comprise a temperature ranging from about 20° C. to about 100° C., total pressures ranging from about 1140 kPaa to about 4240 kPaa (from about 150 psig to about 600 psig), LHSV ranging from about 0.1 to about 100, and a hydrogen/(alkyne+alkadiene) ratio ranging from about 0.1 to about 100 on a molar basis.

In yet another embodiment of this aspect of the invention, the exposing conditions are carried out in the vapor phase and comprise a temperature ranging from about 20° C. to about 600° C., total pressures ranging from about 102 kPaa to about 4240 kPaa (from about 0.1 psig to about 600 psig), GHSV ranging from about 100 to about 20,000, and hydrogen partial pressure ranging from about 0.001 psig to about 200 psig.

In still yet another embodiment of this aspect of the invention, the conversion of the dimethyl ether to at least one higher boiling product is at least about 20%, typically at least about 50%, say, at least about 80%.

In another embodiment of this aspect of the invention, the at least one higher boiling product is formed from the reaction of dimethyl ether with a member selected from the group consisting of the alkyne, the alkadiene and the propylene. Typically, the alkyne comprises methyl acetylene, the alkadiene comprises propadiene, and the higher boiling product is selected from a member selected from the group consisting of acetone and methylisopropyl ether. Additional amounts of a member selected from the group consisting of alkyne and alkadiene can be added as necessary, to react during the exposing with unreacted oxygenate.

In still another embodiment of this aspect of the invention, the exposing is carried out under conditions sufficient to effect at least partial hydrogenation of said member selected from the group consisting of alkyne and alkadiene at a conversion of at least about 20%, typically at least about 50%, say, at least about 80%.

In yet another embodiment of this aspect of the invention, the exposing is carried out under conditions sufficient to effect at least partial hydrogenation of said member selected from the group consisting of alkyne and alkadiene so as to provide a member selected from the group consisting of ethylene, propylene and butene.

In still yet another embodiment of this aspect of the invention, the removing of the higher boiling product is carried out by fractionating in a distillation column.

Another aspect of the invention relates to a process for at least partially removing oxygenate impurities from an olefin-containing stream produced by an oxygenate to olefin process which comprises: contacting an oxygenate feedstream with an olefin conversion catalyst under conditions sufficient to provide a first product stream which contains water, $C_{5+}$ organic compounds, ethylene, propylene, butylenes and oxygenates comprising dimethyl ether, and unsaturated $C_2$ to $C_4$ by-products comprising a member selected from the group consisting of an alkyne and an alkadiene; at least partially removing said water, ethylene, butylenes and $C_{5+}$ organic compounds from said first product stream to provide a second product stream enriched in propylene relative to said first product stream and comprising a member selected from the group consisting of an alkyne and an alkadiene, and containing dimethyl ether; exposing at least a portion of said second product stream in the presence of hydrogen to a hydrogenation catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) a member selected from the group consisting of a porous inorganic oxide and microporous crystalline molecular sieve, said exposing taking place at conditions sufficient to simultaneously effect 1) conversion of said dimethyl ether to at least one higher boiling product, and 2) at least partial hydrogenation of said member selected from the group consisting of alkyne and alkadiene; thereby providing a third product stream; and removing said higher boiling product from said third product stream.

In another aspect of the invention, the present invention relates to a process for at least partially removing from a product stream comprising $C_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethylisopropyl ether, n-propylisopropyl ether, or mixtures thereof which comprises: converting said oxygenate impurity to a compound whose boiling point differs by at least about 5° C. from said oxygenate impurity; and separating at least some of said compound from said $C_x$ olefin. Typically, the converting step is carried out in the presence of $H_2O$ with an acid catalyst under conditions sufficient to at least partially convert said oxygenate impurity to its corresponding alcohol(s).

In one embodiment of this aspect of the invention, the oxygenate impurity is dimethyl ether and the corresponding alcohol is methanol.

In another embodiment of this aspect of the invention, the product stream comprises propane. The propane-containing stream is typically derived from an oxygenate to olefins conversion process effluent.

In still another embodiment of this aspect of the invention, the catalyst is a non-shape selective acid catalyst, e.g., gamma-alumina.

In yet another embodiment of this aspect of the invention, the conditions comprise a temperature ranging from about 300° C. to about 800° C. and a weight ratio of the dimethyl ether to the $H_2O$ of no greater than about 2.5, typically, a temperature of at least about 500° C. and a weight ratio of the dimethyl ether to the $H_2O$ ranging from about 1.2 to about 2.5, say, a temperature ranging from about 600° C. to about 800° C. and a weight ratio of the dimethyl ether to the $H_2O$ ranging from about 0.5 to about 2.5.

In still yet another embodiment of this aspect of the invention, the conditions provide at least about 25% to about 95% conversion of the dimethyl ether to methanol, typically at least about 90% conversion of the dimethyl ether to methanol, say, at least about 92% conversion of said dimethyl ether to methanol.

In another embodiment of this aspect of the invention, at least some of the $H_2O$ is steam.

In still another embodiment of this aspect of the invention, at least some of the $H_2O$ is separated along with said methanol in the separation step.

DETAILED DESCRIPTION OF THE INVENTION

Figure 1:
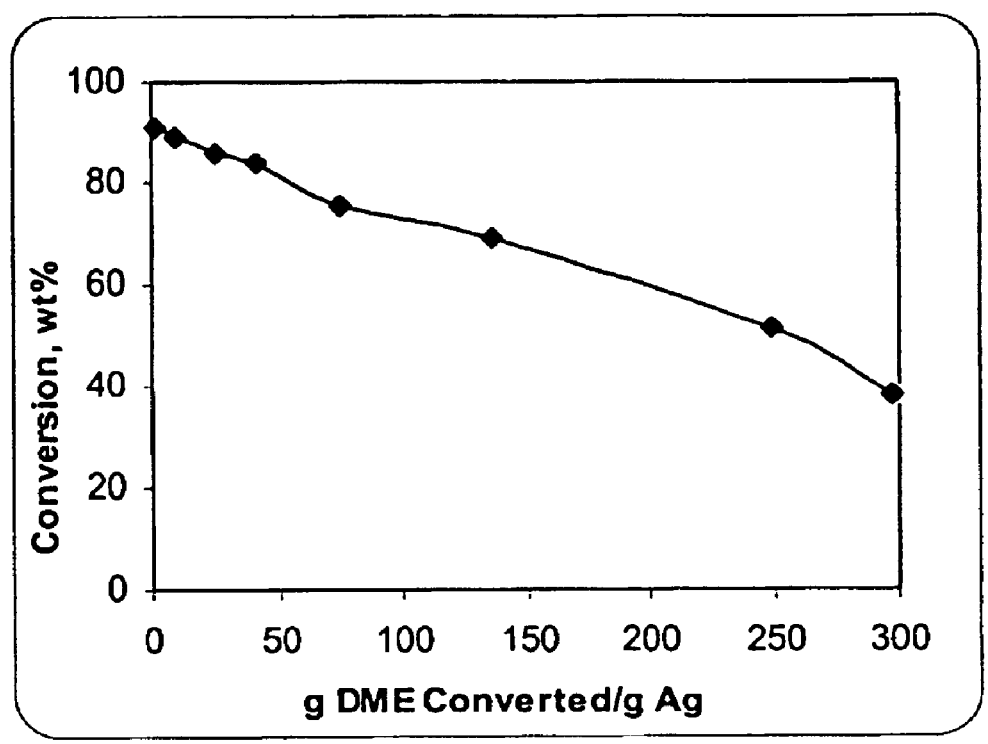
FIG. 1 depicts a plot of dimethyl ether conversion (wt %) versus cumulative grams of dimethyl ether converted per gram of Ag, for dimethyl ether removal via catalytic decomposition.

Oxygenate to Olefin Conversion
Molecular Sieves and Catalysts Thereof

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. No. 4,824, 554, 4,744,970 (COAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

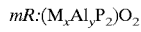
$$mR:(M_xAl_yP_z)O_2$$

wherein R represents at least one templating agent, preferably an organic templating agent; m is the number of moles of R per mole of $(M_xAl_yP_z)_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Oxygenate to Olefin Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R—NH)_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

$(—NHCH_2CH_2—)_m[—N(CH_2CH_2NH_2)CH_2CH_2—]_n)$, wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethyleneimine, ethoxylated polyethyleneimine, polypropylenimine diamine dendrimers (DAB-Am-n), poly(allylamine) $[CH_2CH(CH_2NH_2)]_n$, poly (1,2-dihydro-2,2,4-trimethylquinoline), and poly (dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethyleneimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672, 469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,32 1), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO45 (EP-A-0 229,-295), boron silicates U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Oxygenate To Olefin Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, κ-alumina, ε-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material (s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer.

Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C.

to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspicl, Robert E. Krieger Publishing Company, New York, N.Y. 1977, which are all herein fully incorporated by reference.

The preferred reactor type are riser reactors generally described in *Riser Reactor, Fluidization and Fluid-Particle Systems,* pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor (s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750 ° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $N_2O$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, for reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

A preferred embodiment of a reactor system for the present invention is a circulating fluid bed reactor with continuous regeneration, similar to a modem fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of no greater than 10 carbon atoms per acid site of the molecular sieve in the catalyst, or the formulated catalyst itself. At least a portion of the regenerated catalyst should be returned to the reactor.

Treatment of Olefinic Streams Containing Oxygenate Impurities

As noted above, the conversion of oxygenates to olefins generates by-products whose presence is undesirable for subsequent applications of the collected olefins, particularly for a product stream comprising $C_x$ olefin wherein x is an integer ranging from 2 to 6. Although the separation of many oxygenate impurities, e.g., ketones and aldehydes, from hydrocarbons such as olefins can be capably handled by existing commercial processes, the separation of other oxygenate impurities, e.g., oxygenates selected from at least one of dimethyl ether, diethyl ether, di-n-propyl ether, diisopropyl ether, methylethyl ether, methyl-n-propyl ether, methylisopropyl ether, ethyl-n-propyl ether, ethylisopropyl ether and n-propylisopropyl ether. Dimethyl ether (DME) can be particularly problematic.

Because DME is an oxygenate impurity formed during the conversion of methanol into light olefins which can act as a poison to downstream olefin polymerization catalysts, removal of DMF from oxygenates to olefins product streams is thus highly desirable.

Unfortunately, such removal can be difficult given, inter alia, DME's physical characteristics similar to certain lower olefins, e.g., its similar volatility to propylene. Separation of DME from propylene by distillation, e.g., using a $C_3$ splitter, requires a super fractionation column requiring significant capital investment. Alternatively, DME's difference in solubility from lower olefins can be exploited by using a water wash to remove DME from an olefinic product stream. Unfortunately, given DME's non-polar characteristics, an extensive volume of water would be required in a water wash tower so employed. Given these difficulties it would be desirable to provide a process for removing DME from olefin-containing streams such as those obtained by conversion of oxygenates to olefins, which does not require superfractionation or water washing.

The present invention solves this problem by converting the oxygenate impurity to a compound whose boiling point differs by at least about 5° C., say at least about 10° C., at least about 25° C. or even at least about 50° C. (as measured at atmospheric pressure), from the oxygenate impurity; and thereafter separating at least some of said compound from said $C_x$ olefin. Such separating can be carried out by any suitable method known to one skilled in the art including fractionation, extraction with an inorganic or organic solvent, and further chemical reaction, as well as combinations of these techniques. The present invention contemplates converting the oxygenate impurity of interest to a compound whose boiling point is either lower or higher than the oxygenate impurity. Further details of the invention are provided below.

Olefinic Streams Containing Oxygenate Impurities

The streams contemplated for treatment by the present invention comprise at least one $C_x$ olefin wherein x is an integer ranging from 2 to 6, as well as an oxygenate impurity selected from at least one of dimethyl ether, diethyl ether, di-n-propyl ether, diisopropyl ether, methylethyl ether, methyl-n-propyl ether, methylisopropyl ether, ethyl-n-propyl ether, ethylisopropyl ether and n-propylisopropyl ether, dimethyl ether (DME). Typically, such streams can be prepared by steam cracking of ethylene or derived from oxygenated feedstocks as described above for oxygenate to olefins processes.

Streams contemplated for processing by the present invention can vary greatly in the amount of oxygenate impurity present. Typically such streams comprise at least 1 mppm oxygenate impurity, e.g., dimethyl ether, say, at least about 10, at least about 50, at least about 100, at least about 1000, at least about 10000, or even at least about 25000 mppm oxygenates. In certain embodiments of the invention, such streams contain up to about 30000 mppm, say, up to about 50000 mppm oxygenates, e.g., dimethyl ether.

In one embodiment wherein the product stream treatable by the present invention comprises at least one member selected from the group consisting of methanol, water, CO and $CO_2$, it is advantageous that said product stream be treated to remove at least some of said member, prior to converting of the oxygenate impurity in accordance with the invention. Such an embodiment typically occurs where methanol is a reactant in an oxygenate to olefins process. Unreacted methanol, as well as water, CO and $CO_2$, usually present as methanol conversion by-products, are removed from the product stream by conventional methods, e.g., stripping, distillation, solvent extraction and membrane separation, provide a stream containing no greater than about 1000 mppm methanol, no greater than about 1000 mppm water, no greater than about 1000 mppm CO, and no greater than about 1000 mppm $CO_2$.

In other embodiments, the product stream treatable by the present invention can comprise at least one of a different type of oxygenate impurity from an ether. Such different oxygenate impurities include ethanal, propanal or butanal, or acetone, 2-butanone, or any isomer of pentanone, to name just a few.

Suitable olefinic streams containing oxygenate impurities treated by the present invention can also contain highly unsaturated olefinic by-products which contain a triple bond and/or plural double bonds. Such highly unsaturated olefins include acetylene, methylacetylene (MA) and propadiene (PD). Making olefins from oxygenated feedstocks produces a unique effluent stream that must ultimately be separated and purified to produce the high purity olefin products currently desired. These unsaturated compounds poison polyolefin catalysts, and therefore must be almost completely removed from olefin product streams.

In one embodiment, the product stream comprises highly unsaturated $C_2$ to $C_4$ by-products comprising a member selected from the group consisting of an alkyne and an alkadiene. Additional amounts of a member selected from the group consisting of alkyne and alkadiene can be added as necessary, to react during the oxygenate impurities converting step with unreacted oxygenate impurities. Typically, the alkyne comprises a member selected from the group consisting of acetylene, methyl acetylene, ethyl acetylene and dimethyl acetylene, and the alkadiene comprises a member selected from the group consisting of propadiene, 1,2-butadiene and 1,3-butadiene. Typically, a $C_2$ olefin fraction of the product stream or stream derived therefrom comprises at least 1 mppm of acetylene, a $C_3$ olefins fraction of a product stream or stream derived therefrom comprises at least 1 mppm of methyl acetylene and/or at least 1 mppm of propadiene, while a $C_4$ olefins fraction of the product stream or stream derived therefrom comprises at least 1 mppm of a member selected from the group consisting of ethyl acetylene, dimethyl acetylene, 1,2-butadiene and 1,3- butadiene. The term $C_x$ olefin(s) fraction, where x is an integer ranging from about 2 to about 4 is meant to include a product stream treated by any one or combination of a fractionation tower or towers, including a demethanizer, deethanizer, depropanizer, debutanizer, $C_2$ splitter, and/or $C_3$ splitter, to provide a stream comprising at least 50 wt % of the respective $C_x$ olefin.

In another embodiment, a $C_3$ to $C_4$ olefin fraction of said product stream contains at least about 1 mppm, at least about 10 mppm, at least 100 mppm, at least about 1000 mppm, or even at least about 10000 mppm oxygenate impurity, and at least 50 wt % $C_3$ plus $C_4$ olefin. In certain embodiments, the oxygenate impurity is DME, or comprises at least 1 mppm DME in combination with any other oxygenate impurity.

The process of the present invention is particularly useful in treating propylene-containing product streams which contain oxygenate impurities. Typically, such product streams range from about 50 to about 99.5 wt % propylene, say, from about 60 to about 98 wt % propylene, e.g., from about 70 to about 95 wt % propylene. Oxygenate impurities may be present in the same amounts as described above for other product streams. These propylene-containing streams are particularly amenable to treatments wherein oxygenates are selectively decomposed, i.e., without substantial conversion of olefins, say, no greater than about 20%, no greater than about 10%, no greater than about 5%, no greater than about 1%, or even no greater than about 0.1%, over a catalyst comprising metal and/or metal oxide to provide mixtures comprising alkane(s), CO and $CO_2$, e.g., methane, CO and $CO_2$.

In another embodiment, the present invention is utilized to at least partially remove oxygenate impurities from an olefin-containing stream produced by an oxygenate to olefin process. The oxygenate to olefin process comprises contacting an oxygenate feedstream with olefin generation catalyst, suitable types of which have been described above, under conditions sufficient to provide a product stream which contains $C_2$ to $C_4$ olefins, $C_2$ to $C_4$ paraffins, hydrogen, methane, oxygenates comprising dimethyl ether, and highly unsaturated $C_2$ to $C_4$ by-products comprising a member selected from the group consisting of an alkyne and an alkadiene. Such streams are treated by exposure to a supported metal catalyst under conditions sufficient to convert the dimethyl ether to at least one higher boiling product, as further described below. The $C_3$ to $C_4$ olefins fraction of the product stream or stream derived therefrom contains at least about 1 mppm, at least about 10 mppm, at least about 100 mppm or even at least about 1000 mppm oxygenate impurities comprising dimethyl ether. Alkyne comprises a member selected from the group consisting of acetylene, methyl acetylene, ethyl acetylene and dimethyl acetylene, while the alkadiene comprises at least one of propadiene, 1,2-butadiene and 1,3-butadiene. Typically, the $C_2$ olefin fraction of this product stream or stream derived therefrom comprises at least 1 mppm of acetylene. A $C_3$ olefin fraction of the product stream or stream derived therefrom comprises at least about 1 mppm, at least about 10 mppm, at least about 100 mppm or even at least about 1000 mppm of methyl acetylene and/or at least about 1 mppm, at least about 10 mppm, at least about 100 mppm or even at least about 1000 mppm of propadiene. A $C_4$ olefin fraction of this product stream or stream derived therefrom typically comprises at least about 1 mppm, at least about 10 mppm, at least about 100 mppm or even at least about 1000 mppm of a member selected from the group consisting of ethyl acetylene, dimethyl acetylene and 1,3-butadiene.

In yet another embodiment, the product stream treated by the present invention is an olefin-containing stream containing oxygenate impurities, derived from an oxygenate to olefin process. More particularly, the initial product stream contains water, ethylene, propylene, butylenes, $C_{5+}$ organic compounds, oxygenate impurities comprising dimethyl ether, and unsaturated $C_2$ to $C_4$ by-products comprising a member selected from the group consisting of an alkyne and an alkadiene. Said water, ethylene, butylenes and $C_{5+}$ organic compounds are at least partially removed to provide a second product stream enriched in propylene relative to the initial product stream, say by flash condensation and/or fractional distillation techniques, and comprising a member selected from the group consisting of an alkyne and an alkadiene, and comprising dimethyl ether. The second product stream is exposed in the presence of hydrogen to a hydrogenation catalyst at conditions sufficient to simultaneously effect 1) conversion of said dimethyl ether to at least one higher boiling product, and 2) at least partial hydrogenation of the member selected from the group consisting of alkyne and alkadiene; thereby providing a third product stream which higher boiling product is removed from the third product stream.

Oxygenate Impurity Conversion Catalyst

Although some embodiments of the present invention treat the olefinic stream containing an oxygenate impurity to provide a compound whose boiling point differs from the oxygenate impurity by non-catalytic means, e.g., exposure to temperatures and pressures sufficient to effect oxygenate conversion in the absence of a catalyst, typically a selective catalyst exhibiting oxygenate impurity conversion properties without substantially converting olefinic components is employed in the present invention.

Typically, the present invention utilizes a catalyst comprising a member selected from the group consisting of a metal and a metal compound, including those described above as being useful for oxygenate to olefins conversion. In one embodiment, the catalyst comprises a member selected from the group consisting of a group 3 (IIIA) metal, group 3 (IIIA) metal compound, group 4 (IVA) metal, group 4 (IVA) metal compound, group 5 (VA) metal, group 5 (VA) metal compound, group 6 (VIA) metal, group 6 (VIA) metal compound, group 7 (VIIA) metal, group 7 (VIIA) metal compound, group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, group 11 (IB) metal compound, group 12 (IIB) metal, and group 12 (IIB) metal compound. (Arabic numerals relate to the newer IUPAC 18 column format whilst Roman numerals relate to 1970 IUPAC rules.)

Catalysts have been found useful for the present invention, especially for embodiments wherein oxygenate impurities are converted to lower boiling compounds. Among these are catalysts comprising Group 11 metals, especially Cu and/or Ag, as well as their compounds. Similarly, Group 12 metals, especially Zn, as well as their compounds, as well as Group 1 metals and compounds thereof, e.g., lithium, sodium, and/or potassium, are especially suitable. Typically, such catalysts comprise an inorganic oxide support, e.g., one comprising at least one element selected from the group consisting of silica, alumina, silica-alumina, zirconia, titania, aluminophosphate, and clay. Further details concerning such supports are given above in the discussion of oxygenate conversion catalysts. Preferably, the inorganic oxide comprises alumina. A catalyst comprising silver supported on alumina has been found especially useful for converting oxygenate impurities to lower boiling compounds. Such a catalyst contains from about 0.1 wt % to about 80 wt % silver. Examples of such catalyst are commercially available from Tonen Chemical Corporation, Tokyo, Japan and commercially prepared by N. E. Chemcat Corporation, Tokyo, Japan. The catalyst comprises 2.18 wt % Ag, 0.11 wt % of K with the rest being $Al_2O_3$.

Methanol synthesis catalysts are also especially useful for such purposes. A typical methanol synthesis catalyst comprises copper, zinc oxide and alumina. Such catalysts contain from about 1 wt % to about 95 wt % copper, and from about 1 wt % to about 95 wt % zinc oxide, e.g., 39.75 wt % copper and 16.64 wt % zinc oxide.

Catalysts suited for use in embodiments of the present invention wherein oxygenate impurities are converted to higher boiling compounds include those which function in the presence of hydrogen as well as those that function in the absence of hydrogen. Exemplary of both are hydrogenation catalysts, such as a supported metal catalyst, e.g., supported noble metal catalyst.

Hydrogenation catalysts are especially suited for use in those embodiments of the present invention wherein the stream treated contains highly unsaturated compounds such as alkynes and/or dienes. An example of such a hydrogenation catalyst comprises a hydrogenation catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) a member selected from the group consisting of a porous inorganic oxide (as described above) and microporous crystalline molecular sieve (as described above). Exposure to such catalyst simultaneously effects 1) conversion of said dimethyl ether to at least one higher boiling product, and 2) at least partial hydrogenation of said member selected from the group consisting of alkyne and alkadiene. Preferably, the catalyst comprises at least one member selected from the group consisting of group 10 (VIII) metal, e.g., palladium, which in one embodiment is supported by an inorganic oxide. Alternatively, the catalyst can comprise at least one of i) at least one porous inorganic oxide selected from the group of oxides of elements of groups 2–5, Zn, groups 13, 14 (excluding carbon), and 15 (excluding nitrogen), and ii) at least one microporous crystalline molecular sieve selected from the group consisting of silicates, aluminosilicates, substituted aluminosilicates, aluminophosphates, and substituted aluminophosphates. In yet another embodiment, the catalyst can further comprise iii) a member selected from the group consisting of a sulfur-containing moiety and oxygen-containing moiety. Examples of such catalysts are commercially available under the tradename C31-1-01, from Sud-Chemie of Louisville, Ky., and contain a minimum of 0.03 wt. % palladium supported on alumina.

For those embodiments of the present invention wherein a stream containing alkane is treated, e.g., propane, oxygenate impurities are converted in the presence of $H_2O$, e.g., steam, with an acid catalyst under conditions sufficient to at least partially convert said oxygenate impurity to its corresponding alcohol(s). Typically, the catalyst is a non-shape selective acid catalyst, e.g., alumina. Preferably, the acidic catalyst comprises gamma-alumina. Further, methanol synthesis catalysts, as described above, are useful in this embodiment, as well as combinations of methanol synthesis catalysts with alumina.

The foregoing catalysts employed in converting oxygenate impurities can be deactivated during use and can be at least partially regenerated in accordance with the techniques described above for oxygenate conversion catalysts, as well as any other suitable regeneration technique know to those skilled in the art.

Oxygenate Impurity Conversion Reactors

Suitable oxygenate impurity conversion reactors for converting olefinic streams containing oxygenate impurities in the presence of a catalyst or supported metal catalyst composition of the invention, include a fixed bed reactor or a fluidized bed reactor, desirably a fixed bed reactor. The reactor can be operated isothermally or adiabatically. For those embodiments of the present invention where the highly unsaturated alkynes and alkadienes are hydrogenated to olefins during oxygenate impurity conversion, adiabatic operation of the reactor is preferred.

Oxygenate Impurity Conversion Conditions

In one aspect, the present invention utilizes oxygenate impurity conversion conditions which are sufficient to convert an oxygenate impurity in the treated stream to a compound of differing boiling point from the oxygenate impurity, say by at least about 5° C., at least about 10° C., or even at least about 50° C.

The conversion temperature employed in the conversion of oxygenate impurities of the present invention, specifically within the reactor, is in the range of from about 100° C. to about 1000° C., preferably from about 140° C. to about 500° C., depending upon, among other things, the specific nature of the feedstock and catalyst system employed.

The conversion pressure employed in the conversion of oxygenate impurities in accordance with the present invention, specifically within the reactor system, varies over a wide range including autogenous pressure. The conversion pressure is based on the partial pressure of the feedstock exclusive of any diluent therein. Typically, the conversion pressure employed in the process is in the range of from about 102 kPaa to about 3 MPaa, preferably from about 200 kPaa to about 2 MPaa, depending upon, among other things, the specific nature of the feedstock and catalyst system employed.

The weight hourly space velocity (WRSV), particularly in a process for converting a feedstock containing an olefin and one or more oxygenate impurites in the presence of a supported metal catalyst composition within a reaction zone, is defined as the total weight of the feedstock, i.e., olefins and oxygenate impurities, excluding any diluents to the reaction zone per hour per weight of catalyst (active material, e.g. metal, plus support in the overall composition) in the reaction zone.

Typically, the WHSV ranges from about 0.05 $hr^{-1}$ to about 5000 $hr^{-1}$, preferably from about 0.1 $hr^{-1}$ to about 3000 $hr^{-1}$, more preferably from about 1 $hr^{-1}$ to about 1500 $hr^{-1}$, even more preferably from about 2 $hr^{-1}$ to about 500 $hr^{-1}$, and most preferably from about 2 $hr^{-1}$ to about 50 $hr^{-1}$.

These conditions are typically sufficient to provide conversion of oxygenate impurity without substantially converting olefins present in the stream being treated. By "substantially converting" is meant that no greater than about 5 wt %, no greater than about 1 wt %, or even no greater than about 0.1 wt % of $C_2$ to $C_6$ olefin is converted, singly or in the aggregate. Moreover, these conditions can include the presence or absence of hydrogen depending on the stream being treated and the desired product resulting from conversion of oxygenate impurity. In those embodiments carried out in the presence of hydrogen, partial pressures of hydrogen range from about 101.4 kPaa to about 930 kPaa (about 0.02 to about 120 psig), preferably from about 102.8 kPaa to about 790 kPaa (about 0.2 to about 100 psig), and most preferably from about 115 kPaa to about 650 kPaa (about 2 to about 80 psig). In cases wherein the treated stream contains a member selected from the group consisting of alkyne and alkadiene, at least partial hydrogenation of a member selected from the group consisting of alkyne and alkadiene can be by at least about 10%, at least about 25%, or even at least about 50%. Such products of the at least partial hydrogenation are selected from at least one of ethylene, propylene, and butenes.

In the present invention, particularly embodiments wherein lower boiling compounds are produced, oxygenate impurity converting can be carried out under conditions sufficient to convert oxygenate impurities, e.g., dimethyl ether, at temperatures ranging from about 300° to about 550° C., and pressures ranging from about 60 kPaa to about 3500 kPaa.

In the present invention, particularly embodiments wherein higher boiling compounds are produced, oxygenate impurity converting can be carried out in the liquid phase and comprises a temperature ranging from about 0° C. to about 100° C., total pressures ranging from about 790 kPaa to about 7 MPaa (from about 100 psig to about 1000 psig), LHSV ranging from about 0.001 to about 1000, and a hydrogen/(alkyne+alkadiene) ratio ranging from about 0.01 to about 1000 on a molar basis, preferably comprising a temperature ranging from about 20° C. to about 80° C., total pressures ranging from about 1140 kPaa to about 4240 kPaa (from about 150 psig to about 600 psig), LHSV ranging from about 0.1 to about 100, and a hydrogen/(alkyne+alkadiene) ratio ranging from about 0.1 to about 100 on a molar basis.

Alternatively, the converting of oxygenate impurity can be carried out in the vapor phase and comprises a temperature ranging from about 0° C. to about 800° C., total pressures ranging from about 101.4 kPaa to about 7 MPaa (from about 0.01 psig to about 1000 psig), GHSV (gas hourly space velocity) ranging from about 10 to about 30,000, and a hydrogen partial pressure ranging from about 101.3 kPaa to about 2170 kPaa (from about 0.001 psig to about 300 psig), preferably comprising a temperature ranging from about 20° to about 600° C., total pressures ranging from about 102.8 kPaa to about 4240 kPaa (from about 0.2 psig to about 600 psig), GHSV ranging from about 100 to about 20,000, and hydrogen partial pressure ranging from about 101.4 kPaa to about 1480 kPaa (ranging from about 0.01 psig to about 200 psig).

Typically, conversion of oxygenate impurities in a treated stream according to the present invention, can be at least about 10%, at least about 20%; at least about 50%, at least about 80%, or even at least about 90%, especially for dimethyl ether conversion, and especially in those instances wherein oxygenate impurity is converted to higher boiling compounds.

Embodiments of the present invention wherein converting of oxygenate impurity, e.g., dimethyl ether, is carried out in the presence of $H_2O$ with acid catalyst to convert oxygenate impurity to its corresponding alcohol(s), typically utilize conditions which comprise a temperature ranging from about 300° C. to about 800° C. and a weight ratio of said dimethyl ether to said $H_2O$ of no greater than about 2.5. Preferably such conditions comprise a temperature of at least about 5000 C. and a weight ratio of said dimethyl ether to said $H_2O$ ranging from about 1.2 to about 2.5. More preferably these conditions comprise a temperature ranging from about 600° C. to about 800° C. and a weight ratio of said dimethyl ether to said $H_2O$ ranging from about 0.5 to about 2.5. Such conditions typically provide at least 25% to 95% conversion of said dimethyl ether to methanol; in one embodiment, such conditions provide at least about 90% or even at least about 92% conversion of said dimethyl ether to methanol.

Separation Methods

Various conventional separation methods known in the art are suitable for separating at least some of the compound of differing boiling point made by converting oxygenate impurity in the presence of olefin, in accordance with the present invention.

In one aspect of the invention, such separation is carried out by utilizing differences in volatility, e.g., boiling point, between oxygenate impurity and conversion products thereof. Exemplary of such methods include fractionation, e.g., with a distillation column, or the use of a simple vapor-liquid disengaging drum (a flash drum).

In another aspect of the invention, differences in solubility between oxygenate impurity and conversion products thereof in aqueous and/or non-aqueous solvents can be relied upon to effect separation, e.g., solvent extraction.

In yet another aspect of the invention, differences in molecular size, shape, polarity, etc. are utilized to effect the desired separation , e.g., membrane separation or molecular sieve adsorption techniques.

Oxygenate Impurity Depleted Treated Streams

A primary effect of the separation step of the present invention is to provide an oxygenate impurity depleted stream. One embodiment of the present invention provides an oxygenate impurity depleted stream which comprises no greater than about 100 mppm, no greater than about 50 mppm, no greater than about 25 mppm, no greater than about 10 mppm, or even no greater than about 1 mppm oxygenate, e.g., dimethyl ether.

For ethylene, current manufacturing specifications can require acetylene levels to be under 0.5 mole ppm. For propylene, current manufacturing specifications can require methyl acetylene and propadiene levels to be under 2.9 mole ppm. The present invention provides an effective way to provide such purified propylene and ethylene products.

The following examples illustrate, but do not limit, the present invention.

EXAMPLES

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

Examples 1 to 5

Oxygenate Impurity Removal by Catalytic Decomposition

Experimental Details

Catalyst testing was carried out in a tubular micro flow-reactor at 450° C. Reagents, e.g., DME, olefins or a mixture of both, were introduced into the reactor via pulses. The size of a typical pulse was 500 or 100 microliters (at 21° C. and 1 atm). The reagent pulses were introduced into the reactor via He carrier gas, the flow rate of which was 72 ml/min. The total reactor pressure was kept constant at 25 psig.

The effluent from the tubular reactor was collected and analyzed by on-line gas chromatography (Hewlett Packard 6890) equipped with both a flame ionization detector and a mass detector. The chromatographic column used was a 150 meter, 0.25 mm (inner diameter) fused silica capillary column (Model No. Petrocol DH 150). Products detectable by FID were quantified. FID-invisible products, such as CO and $CO_2$, were detected by a mass detector. However, no efforts were made to quantify the FID-invisible products. Inasmuch as the conversions reported below were based on the FID signals, neglecting the FID-invisible products, the reported conversions for DME were lower than actual conversions.

Two catalysts were used in screening tests for decomposing DME, i.e., a supported silver catalyst and a methanol synthesis catalyst. The supported silver catalyst comprises 2.18 wt % Ag, 0.11 wt % of K with the rest being $Al_2O_3$. The methanol synthesis catalyst contains 16.64 wt % Zn and 39.75 wt % Cu.

Example 1

Fifty mg of the supported silver catalyst were mixed with one g of silicon carbide. The mixture was packed into the tubular reactor and was heated up to 450° C. under He flow. One hundred microliter pulses of dimethyl ether were introduced into the reactor after the reactor temperature stabilized at 450° C. Analysis of the products exiting the reactor revealed the conversion of DME was 95 wt % or greater. The main products were methane, CO and $CO_2$ as qualified by a mass detector.

Example 2

The reactivity of typical olefins from a methanol-to-olefins reactor, i.e., propene and butenes, was studied at 450° C. with 100 microliter pulses of olefin. Fifty mg of the supported silver catalyst were mixed with one g of silicon carbide. The mixture was packed into the tubular reactor and was heated up to 450° C. under He flow. One hundred-microliter pulses of propene were introduced into the reactor after the reactor temperature stabilized at 450° C. Analysis of the products exiting the reactor revealed that less than 0.5 wt % of propene was converted on the supported silver catalyst under the same reaction conditions as those shown in Example 1. The main product was propane.

Some reactions were observed for 1-butene after passing through 150 mg of catalyst at 450° C., and the results are summarized in TABLE 1 below, which sets out typical product distribution in wt %. One hundred fifty mg of the supported silver catalyst were mixed with one g of silicon carbide. The mixture was packed into the tubular reactor and was heated up to 450° C. under He flow. One thousand-microliter pulses of 1-butene were introduced into the reactor after the reactor temperature stabilized at 450° C. Analysis of the products exiting the reactor revealed that 1-butene was isomerized to form cis- and trans-butenes. Isomerization reactions are believed to be induced on the surface of the support, i.e., $Al_2O_3$. A lower level of butadiene was also observed in the products as a result of the dehydrogenation reaction of butenes.

TABLE 1

| Pulses | 1-Butene | Butadiene | Butane | Trans-2-butene | Cis-2-butene |
|---|---|---|---|---|---|
| 1 | 26.5 | 2.7 | 0.4 | 39.5 | 29.0 |
| 2 | 26.7 | 0.9 | 0.4 | 40.9 | 30.0 |
| 3 | 27.1 | 0.7 | 0.3 | 41.6 | 29.8 |
| Average | 26.6 | 1.4 | 0.4 | 40.7 | 29.6 |
| Std. Deviation | 0.3 | 1.1 | 0.0 | 1.1 | 0.5 |

Example 3

Fifty mg of the supported silver catalyst were mixed with one gram of silicon carbide. The mixture was packed into the tubular reactor and was heated up to 450° C. under He flow. Five hundred-microliter pulses of a mixture of DME and propene (39 wt % DME+57 wt % propene) were introduced into the reactor after the reactor temperature stabilized at 450 ° C. The results indicate that the conversion of dimethyl ether to methane, CO and $CO_2$ was greater than 98 wt %.

Example 4

Supported silver catalyst (1.1 g) was loaded into a tubular reactor and was heated to 450° C. under He flow. The reactor temperature was maintained at 450° C. for one hour. The reactor temperature was then reduced to 350° C. A mixture of 12 ml/min $H_2$ and 56 ml/min He was flowed through the catalyst at 350° C. for 3 hrs. Elemental analysis of thus-treated catalyst revealed that the treated catalyst contains 1.94 wt % of Ag.

Fifty mg of the treated catalyst were mixed with one g of silicon carbide. The mixture was packed into the tubular reactor and was heated up to 450° C. under He flow. Five hundred-microliter pulses of DME were introduced into the reactor after the reactor temperature stabilized at 450° C. FIG. 1 shows a plot of DME conversion (wt %) as a function of gram of cumulatively converted DME per gram of Ag. The results indicate that the catalyst gradually deactivated as the amount of DME converted increased. After about 249 g of dimethyl ether were converted per gram of Ag, the conversion fell to about 50 wt %.

Example 5

Fifty mg of the methanol synthesis catalyst were mixed with one g of silicon carbide. The mixture was packed into the tubular reactor and was heated up to 450° C. under He flow. One hundred-microliter pulses of DME were introduced into the reactor after the reactor temperature stabilized at 450° C. Analysis of the products exiting the reactor revealed the conversion of DME was about 10 wt %.

Example 6

Conversion of Oxygenate Impurities in the Presence of Highly Unsaturated Olefin A feed comprising dimethyl ether, methyl acetylene, and propadiene was exposed to a commercial gas-phase methyl acetylene/propadiene (MAPD) hydrogenation catalyst obtained from SCI of Louisville, Ky., USA. The catalyst was reduced under hydrogen at 232° C. (450° F.) and 360 GHSV and then cooled to reaction temperature under helium flow. Hydrocarbon was fed to the reactor at a rate of 3.2 WHSV with respect to total catalyst weight (960 GHSV, with respect to total catalyst volume). The feed consisted of 84.13 mol % propylene, 9.56 mol % propane, 2.63 mol % methyl acetylene, 3.68 mol % propadiene and 183 ppm dimethyl ether. Hydrogen was co-fed to attain varying $H_2$/MAPD (hydrogen to methyl acetylene and propadiene) molar ratios.

TABLE 2 shows a typical hydrocarbon product distribution at 209° C. and approximately 310 psig. Under these conditions, MAPD conversion was about 87 mol %. In addition, a DME conversion of about 50 mol % was attained.

Major oxygenate products included acetone and methyl isopropyl ether, which could be easily separated from light olefins in a depropanizer distillation column. TABLE 3 shows a product distribution from the converted DME.

TABLE 2

Reaction Conditions and Product Distribution from MAPD Conversion

| | |
|---|---|
| WRSV (h$^{-1}$) | 3.2 |
| Temperature (° C.) | 209 |
| Pressure kPaa (psig) | 2240 |
| | (309.6) |
| H$_2$/MAPD (mol) | 1.10 |
| FEED (mol % except as noted) | |
| C$_3$ = | 84.13 |
| C$_3$ | 9.56 |
| Methyl Acetylene | 2.63 |
| Propadiene | 3.68 |
| DME (ppm) | 183 |
| PRODUCT | |
| C$_1$ | 0.00 |
| C$_2$ = | 0.05 |
| C$_2$ | 0.01 |
| C$_3$ | 11.26 |
| Methyl Acetylene | 0.26 |
| Propadiene | 0.56 |
| iC$_4$ and nC$_4$ | 0.03 |
| C$_4$ = | 0.03 |
| C$_4$ == | 0.04 |
| C$_5$s | 0.02 |
| C$_6$s | 0.26 |
| Benzene | 0.00 |
| C$_6$s + | 0.08 |
| DME (ppm) | 93 |
| Estimated Oxygenates (ppm) | 90 |

TABLE 3

Distribution of Oxygenated Products

| Oxygenate Product | Selectivity (mol %) |
|---|---|
| Methyl Isopropyl Ether | 56.7 |
| Acetone | 27.7 |
| Isopropanol | 7.1 |
| Methanol | 5.4 |
| Diisopropyl Ether | 3.2 |

Example 7

Conversion of Oxygenate Impurities in Presence of Propane and Olefin

Figure 2:
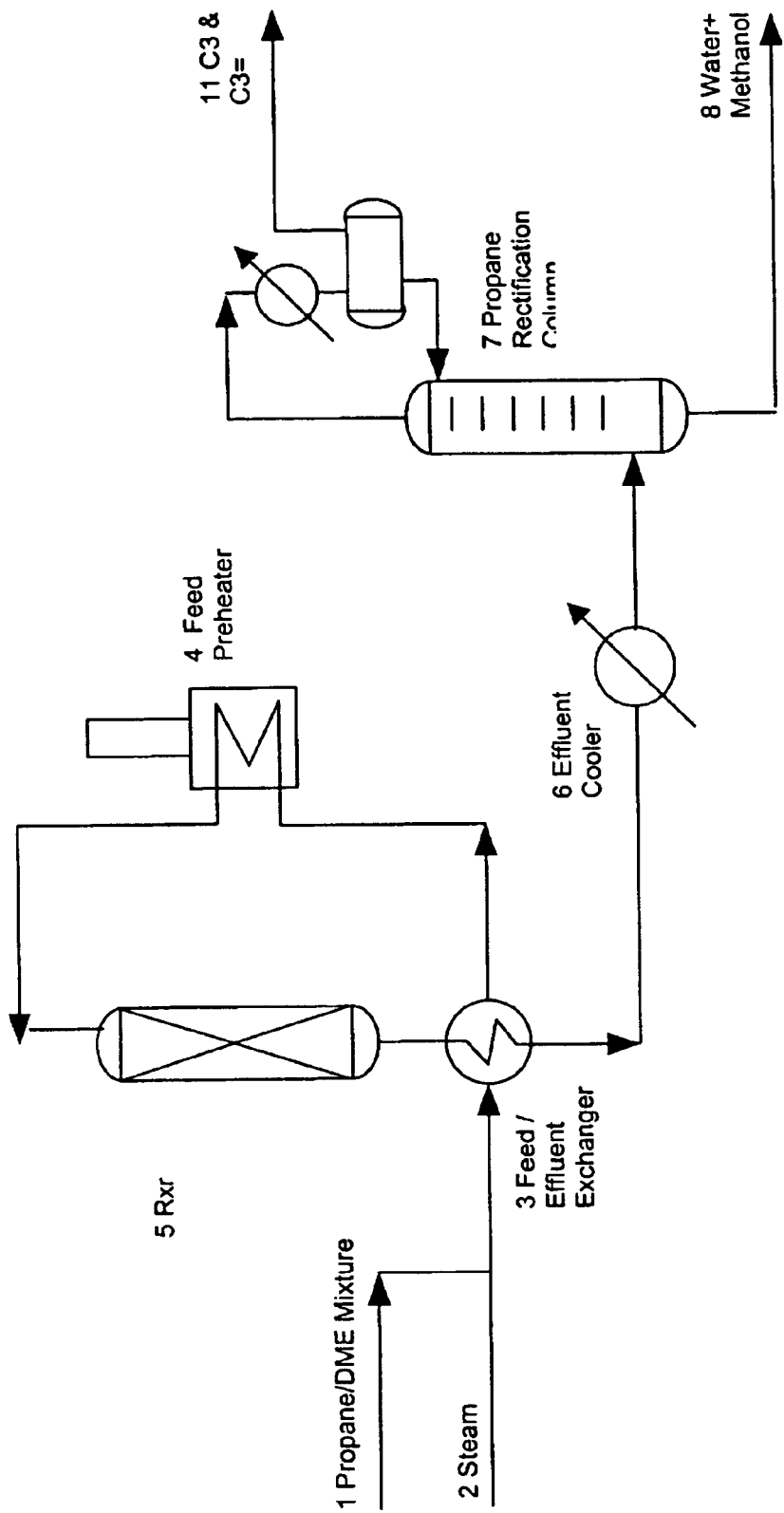
FIG. 2 depicts a process scheme for removing oxygenate (DME) from an olefinic stream.

As depicted in FIG. 2, a mixture containing propane, dimethyl ether and propene in a molar ratio of 1.5/3.0/40.0 is fed through line 1 and combined with steam in line 2, preheated through feed/effluent exchanger and feed preheater 4 and thence to reactor 5. Hot reaction products exit the reactor and pass through feed/effluent exchanger 3, effluent cooler 6 and pass through propane rectification column 7 whence water and methanol are recovered as bottoms through line 8. Overhead containing propane and propene passes via propane rectification effluent cooler 9 to a vapor liquid disengaging drum 10 from which propane and propene vapor are recovered via line 11 and liquid propane and propene are cycled to propane rectification column 7. Reactor 5 is maintained at conditions which comprise temperatures ranging from 300° to 800° C., wherein a vapor stream comprising propane and dimethyl ether is contacted with a gamma alumina catalyst to convert the dimethyl ether to methanol.

Figure 3:
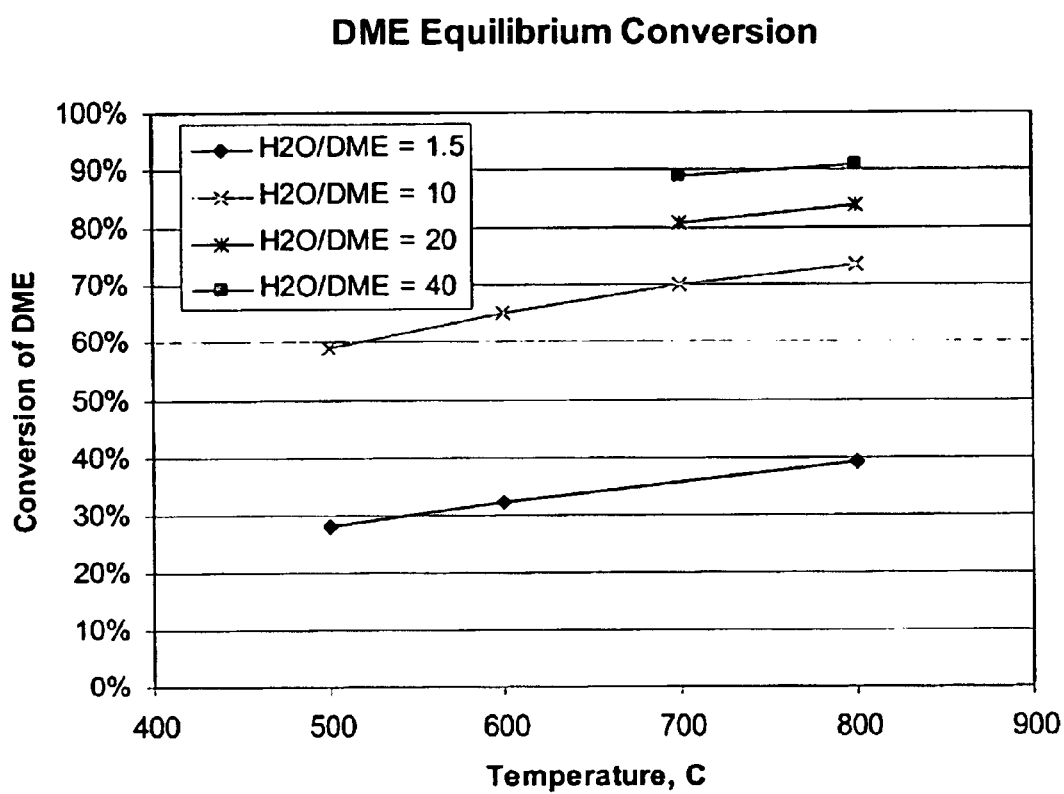
FIG. 3 depicts DME equilibrium conversion versus temperature for mixtures of water and dimethyl ether

The water and dimethyl ether react to form methanol without converting propane or propene, up to the thermodynamic equilibrium constraint as shown in FIG. 3, given for H$_2$O DME weight ratios ranging from 1.5 to 40.

The equilibrium conversion is seen to be favored by high reaction temperatures and excess water. The reaction pressure thus appears to have little effect on the equilibrium conversion. As shown by FIG. 3, a more than 90% conversion of DME to methanol can be achieved by operating the reactor feed temperature at 800° C. with a 40:1 weight ratio of water to DME in the feed. This treatment is particularly useful for processing streams comprising major amounts of propane and oxygenate impurities, e.g., dimethyl ether, relative to olefin content, say, e.g., streams comprising 1 to 10 wt % propane, 5 to 20 wt % dimethyl ether and 5 to 20 wt % olefins, e.g., propene.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

We claim:

1. A process for at least partially removing from a product stream comprising C$_x$ olefin wherein x is an integer ranging from 2 to 6, an oxygenate impurity selected from dimethyl ether, diethyl ether, di-n-propyl ether, diisopropyl ether, methylethyl ether, methyl-n-propyl ether, methylisopropyl ether, ethyl-n-propyl ether, ethylisopropyl ether and n-propylisopropyl ether, which comprises:

converting said oxygenate impurity to a compound whose boiling point differs by at least about 5° C. from said oxygenate impurity; and separating at least some of said compound from said C$_x$ olefin.

2. The process of claim 1 wherein said oxygenate impurity is dimethyl ether.

3. The process of claim 2 wherein said product stream comprises at least about 1 mppm dimethyl ether.

4. The process of claim 2 wherein said product stream comprises at least about 2.5 wt % dimethyl ether.

5. The process of claim 2 wherein said separating provides an oxygenate impurity-depleted stream which comprises no greater than about 100 mppm dimethyl ether.

6. The process of claim 2 wherein said separating provides an oxygenate impurity-depleted stream which comprises no greater than about 50 mppm dimethyl ether.

7. The process of claim 2 wherein said separating provides an oxygenate impurity-depleted stream which comprises no greater than about 10 mppm dimethyl ether.

8. The process of claim 2 wherein said separating provides an oxygenate impurity-depleted stream which comprises no greater than about 1 mppm dimethyl ether.

9. The process of claim 2 wherein said product stream comprises propylene.

10. The process of claim 1 wherein said separating is carried out by fractionating in a distillation column.

11. The process of claim 1 wherein said converting is carried out without substantially converting said C$_x$ olefin.

12. The process of claim 1 wherein said converting is carried out in the absence of added hydrogen.

13. The process of claim 1 wherein said converting is carried out in the presence of added hydrogen.

14. The process of claim 1 wherein said product stream comprises at least one member selected from the group consisting of methanol, water, CO and CO$_2$, wherein said product stream is treated to remove at least some of said member, prior to said converting.

15. The process of claim 1 wherein said product stream containing said oxygenate impurity is derived from a process which converts oxygenates to olefins.

16. The process of claim 1 wherein said boiling point differs by at least about 10° C.

17. The process of claim 1 wherein said boiling point differs by at least about 50° C.

18. The process of claim 1 wherein said boiling point of said compound is at least about 5° C. lower than said oxygenate impurity.

19. The process of claim 18 wherein said converting step comprises contacting at least a portion of said hydrocarbonaceous stream with a catalyst comprising a member selected from the group consisting of metal and metal compound.

20. The process of claim 19 wherein said catalyst comprises at least one member selected from the group consisting of group 3 (IIIA) metal, group 3 (IIIA) metal compound, group 4 (IVA) metal, group 4 (IVA) metal compound, group 5 (VA) metal, group 5 (VA) metal compound, group 6 (VIA) metal, group 6 (VIA) metal compound, group 7 (VIIA) metal, group 7 (VIIA) metal compound, group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group II (IB) metal, group 11 (IB) metal compound, group 12 (IIB) metal, and group 12 (IIB) metal compound.

21. The process of claim 19 wherein said oxygenate impurity comprises dimethyl ether and said converting is carried out under conditions sufficient to convert said dimethyl ether to a mixture containing a member selected from the group consisting of methane, CO and $CO_2$.

22. The process of claim 19 wherein said catalyst comprises at least one member selected from the group consisting of group 11 (IB) metal and group 11 (IB) metal compound.

23. The process of claim 22 wherein said catalyst comprises Ag or a compound thereof.

24. The process of claim 19 wherein said catalyst comprises at least one of a group 11 (IB) metal or metal compound, and at least one inorganic oxide.

25. The process of claim 24 wherein said catalyst further comprises a group 12 (IIB) metal or metal compound.

26. The process of claim 25 wherein said catalyst further comprises a group 1 (IA) metal or metal compound.

27. The process of claim 26 wherein said group 11 (IB) metal or metal compound is selected from the group consisting of copper and copper compounds.

28. The process of claim 24 wherein said group 11 (IB) metal or metal compound is selected from the group consisting of silver and silver compounds.

29. The process of claim 24 wherein said inorganic oxide support comprises a member selected from the group consisting of silica, alumina, silica-alumina, zirconia, titania, aluminophosphate, and clay.

30. The process of claim 24 wherein said inorganic oxide comprises alumina.

31. The process of claim 24 wherein said catalyst comprises silver supported on alumina.

32. The process of claim 21 wherein said catalyst is a methanol synthesis catalyst.

33. The process of claim 32 wherein said methanol synthesis catalyst comprises copper, zinc oxide and alumina.

34. The process of claim 18 wherein no greater than about 1 wt % of said $C_x$ olefin is converted by said converting step.

35. The process of claim 18 wherein no greater than about 0.1 wt % of said $C_x$ olefin is converted by said converting step.

36. The process of claim 21 wherein said conditions sufficient to convert said dimethyl ether comprise temperatures ranging from about 300° to about 550° C., and pressures ranging from about 60 to about 3500 kPaa.

37. The process of claim 1 wherein said boiling point of said compound is at least about 10° C. lower than said oxygenate impurity.

38. The process of claim 1 wherein said boiling point of said compound is at least about 50° C. lower than said oxygenate impurity.

39. The process of claim 1 wherein said boiling point of said compound is at least about 5° C. higher than said oxygenate impurity.

40. The process of claim 39 wherein said converting is carried out in the absence of added hydrogen.

41. The process of claim 39 wherein said converting is carried out in the presence of added hydrogen.

42. The process of claim 39 wherein said converting comprises contacting at least a portion of said product stream with a supported metal catalyst comprising i) at least one member selected from the group consisting of group 8 (VIIIA) metal, group 8 (VIIIA) metal compound, group 9 (VIIIA) metal, group 9 (VIIIA) metal compound, group 10 (VIIIA) metal, group 10 (VIIIA) metal compound, group 11 (IB) metal, and group 11 (IB) metal compound, of the Periodic Table, and ii) at least one of a porous inorganic oxide and microporous crystalline molecular sieve, said converting taking place at conditions sufficient to convert said oxygenate impurity to at least one higher boiling compound.

43. The process of claim 42 wherein said contacting is carried out in the presence of hydrogen and said supported metal catalyst is a hydrogenation catalyst.

44. The process of claim 42 wherein said contacting is carried out in the absence of hydrogen.

45. The process of claim 42 said product stream comprises highly unsaturated $C_2$ to $C_4$ by-products comprising a member selected from the group consisting of an alkyne and an alkadiene.

46. The process of claim 42 wherein additional amounts of a member selected from the group consisting of alkyne and alkadiene are added as necessary, to react during said converting with unreacted oxygenate.

47. The process of claim 42 wherein said alkyne comprises a member selected from the group consisting of acetylene, methyl acetylene, ethyl acetylene and dimethyl acetylene, and said alkadiene comprises a member selected from the group consisting of propadiene, 1,2-butadiene and 1,3-butadiene.

48. The process of claim 42 wherein the $C_2$ olefin fraction of said product stream or stream derived therefrom comprises at least 1 mppm of acetylene.

49. The process of claim 42 wherein the $C_3$ olefins fraction of said product stream or stream derived therefrom comprises at least 1 mppm of methyl acetylene and/or at least 1 mppm of propadiene.

50. The process of claim 42 wherein the $C_4$ olefins fraction of said product stream or stream derived therefrom comprises at least 1 mppm of a member selected from the group consisting of ethyl acetylene, dimethyl acetylene, 1,2-butadiene and 1,3-butadiene.

51. The process of claim 43 wherein said converting provides at least partial hydrogenation of said a member selected from the group consisting of alkyne and alkadiene by at least about 20%.

52. The process of claim 43 wherein said at least partial hydrogenation provides a member selected from the group consisting of ethylene, propylene and butene.

53. The process of claim 43 wherein said oxygenate impurity comprises dimethyl ether.

54. The process of claim 53 wherein wherein said product stream comprises $C_3$ to $C_4$ olefins and at least about 1 mppm oxygenate impurity.

55. The process of claim 54 wherein said catalyst comprises at least one member selected from the group consisting of group 10 (VIII) and group 11 (IB) metals.

56. The process of claim 42 wherein said catalyst comprises palladium.

57. The process of claim 42 wherein said catalyst comprises palladium and silver.

58. The process of claim 42 wherein said catalyst comprises at least one of i) at least one porous inorganic oxide selected from the group consisting of silica, alumina, silica-alumina, zirconia, titania, aluminophosphate and clay, and ii) at least one microporous crystalline molecular sieve selected from the group consisting of silicates, aluminosilicates, substituted aluminosilicates, aluminophosphates, and substituted aluminophosphates.

59. The process of claim 58 wherein said catalyst further comprises iii) at least one of a sulfur-containing moiety and oxygen-containing moiety.

60. The process of claim 42 wherein said converting is carried out in the liquid phase and comprises a temperature ranging from about 20° C. to about 100° C., total pressures ranging from about 1140 kPaa to about 4240 kPaa (from about 150 psig to about 600 psig), LHSV ranging from about 0.1 to about 100, and a hydrogen/(alkyne+alkadiene) ratio ranging from about 0.1 to about 100 on a molar basis.

61. The process of claim 42 wherein said converting is carried out in the vapor phase and comprise a temperature ranging from about 20° C. to about 600° C., total pressures ranging from about 102 kPaa to about 4240 kPaa (from about 0.1 psig to about 600 psig), GHSV ranging from about 100 to about 20,000, and hydrogen partial pressure ranging from about 0.001 psig to about 200 psig.

62. The process of claim 53 wherein said higher boiling compound is selected from the group consisting of acetone and methyl isopropyl ether.

63. The process of claim 53 wherein at least about 20% of said dimethyl ether in the product stream is converted during said converting step.

64. The process of claim 53 wherein at least about 50% of said dimethyl ether in the product stream is converted during said converting step.

65. The process of claim 53 wherein at least about 80% of said dimethyl ether in the product stream is converted during said converting step.

66. The process of claim 1 wherein said boiling point of said compound is at least about 10° C. higher than said oxygenate impurity.

67. The process of claim 1 wherein said boiling point of said compound is at least about 50° C. higher than said oxygenate impurity.

68. A process for at least partially removing dimethyl ether from a propylene-containing olefins stream which comprises converting at least a portion of said stream over a catalyst comprising metal and/or metal oxide, under conditions sufficient to selectively decompose said dimethyl ether to a mixture of methane, CO and $CO_2$, in the presence of said olefins without substantially converting said olefins.

69. The process of claim 68 wherein said catalyst comprises silver supported on alumina.

70. The process of claim 68 wherein said catalyst comprises copper, zinc oxide and alumina.

71. The process of claim 68 wherein said converting step is carried out in the absence of added hydrogen.

* * * * *